(12) United States Patent
Artal

(10) Patent No.: US 6,428,318 B2
(45) Date of Patent: Aug. 6, 2002

(54) DENTAL IMPLANT AND OPERATIVE METHOD OF IMPLANTATION

(75) Inventor: Alberto Arruga Artal, Monasterio de Samos, 15 -1°A, 50008 Zaragoza (ES)

(73) Assignees: Alberto Arruga Artal; Carlos Arruga Artal, both of Saragossa (ES)

( * ) Notice: Subject to any disclaimer, the term of this patent is extended or adjusted under 35 U.S.C. 154(b) by 0 days.

(21) Appl. No.: 09/823,090

(22) Filed: Mar. 30, 2001

(30) Foreign Application Priority Data

Apr. 14, 2000 (ES) .......................................... 200000984

(51) Int. Cl.$^7$ ................................................. A61C 8/00
(52) U.S. Cl. .................... 433/173; 433/174; 433/201.1; 206/63.5
(58) Field of Search ................................ 433/172, 173, 433/174, 175, 176, 201.1; 206/63.5

(56) References Cited

U.S. PATENT DOCUMENTS

| | | | | |
|---|---|---|---|---|
| 4,689,014 A | * | 8/1987 | Krasner | 433/215 |
| 4,808,184 A | * | 2/1989 | Tepic | 433/201.1 |
| 4,820,306 A | * | 4/1989 | Gorman et al. | 433/201.1 |
| 5,087,199 A | * | 2/1992 | Lazarof | 433/173 |
| 5,538,428 A | * | 7/1996 | Staubli | 433/173 |
| 5,961,330 A | * | 10/1999 | Hanson | 433/173 |
| 6,190,412 B1 | * | 2/2001 | Lee et al. | 623/16.11 |

* cited by examiner

Primary Examiner—John J. Wilson
(74) Attorney, Agent, or Firm—Klauber & Jackson

(57) ABSTRACT

Dental implant and operative method of implantation, being of the type of implant comprising a body that is threaded into the jawbone via which the appropriate securing and fastening bodies for the dental prosthesis are located, the implant body (1) displaying an axial cavity (2) along its entire length, and whose internal base for implantation displays certain drilled holes and/or angular cuts (3) in its lateral surface that define end tabs, the implants being presented individually in their respective sterilized receptacles (5), being joined to the cap body (6) of the receptacle (5) via an intermediate body (7), the cap body (6) defining a cavity (11) with respect to its external base, in which is housed a body (12) made of rubber or similar material.

6 Claims, 2 Drawing Sheets

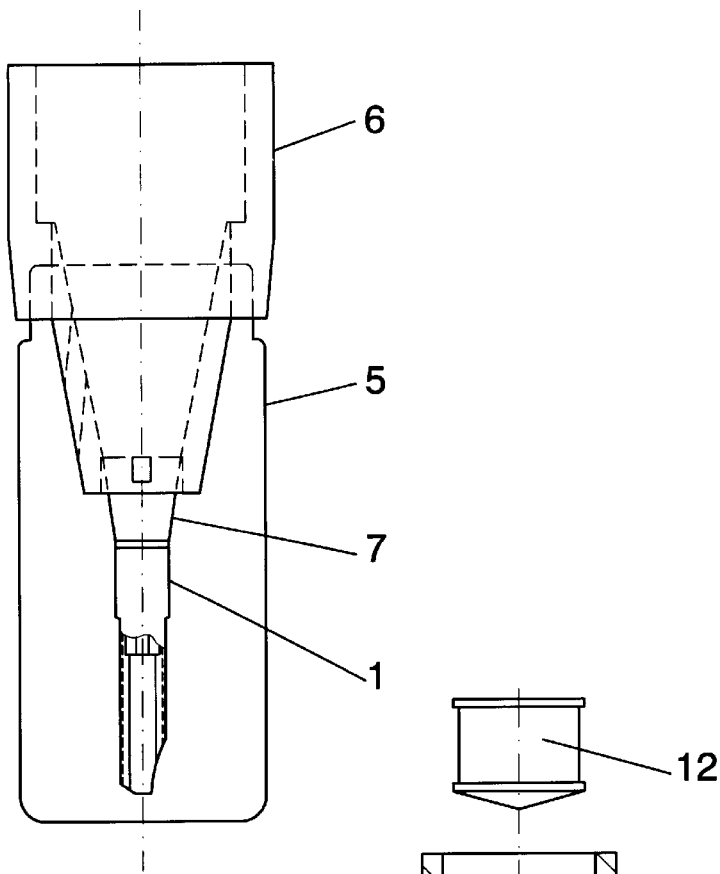
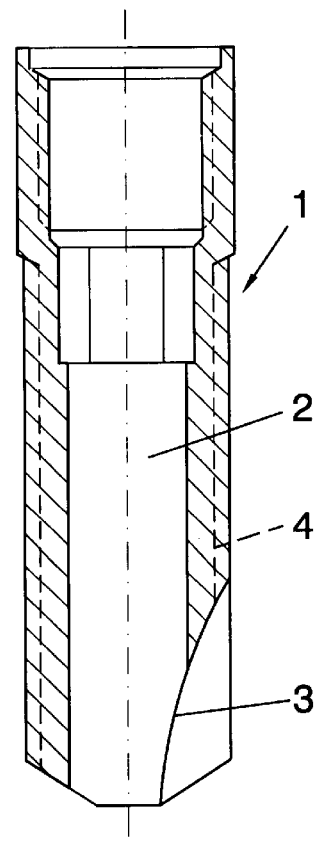
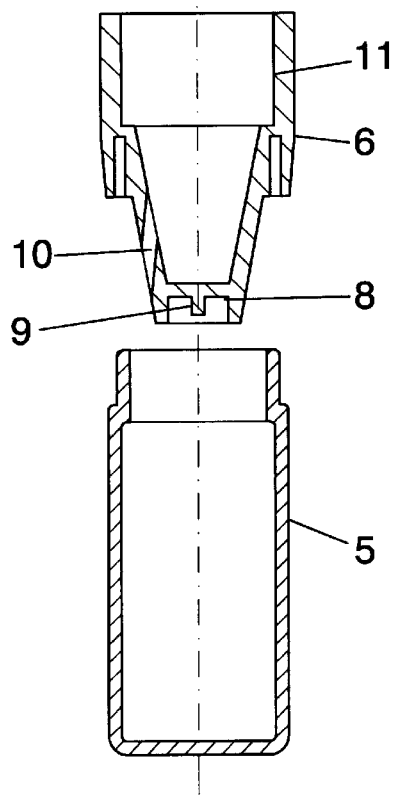
Fig. 1
Fig. 2
Fig. 3

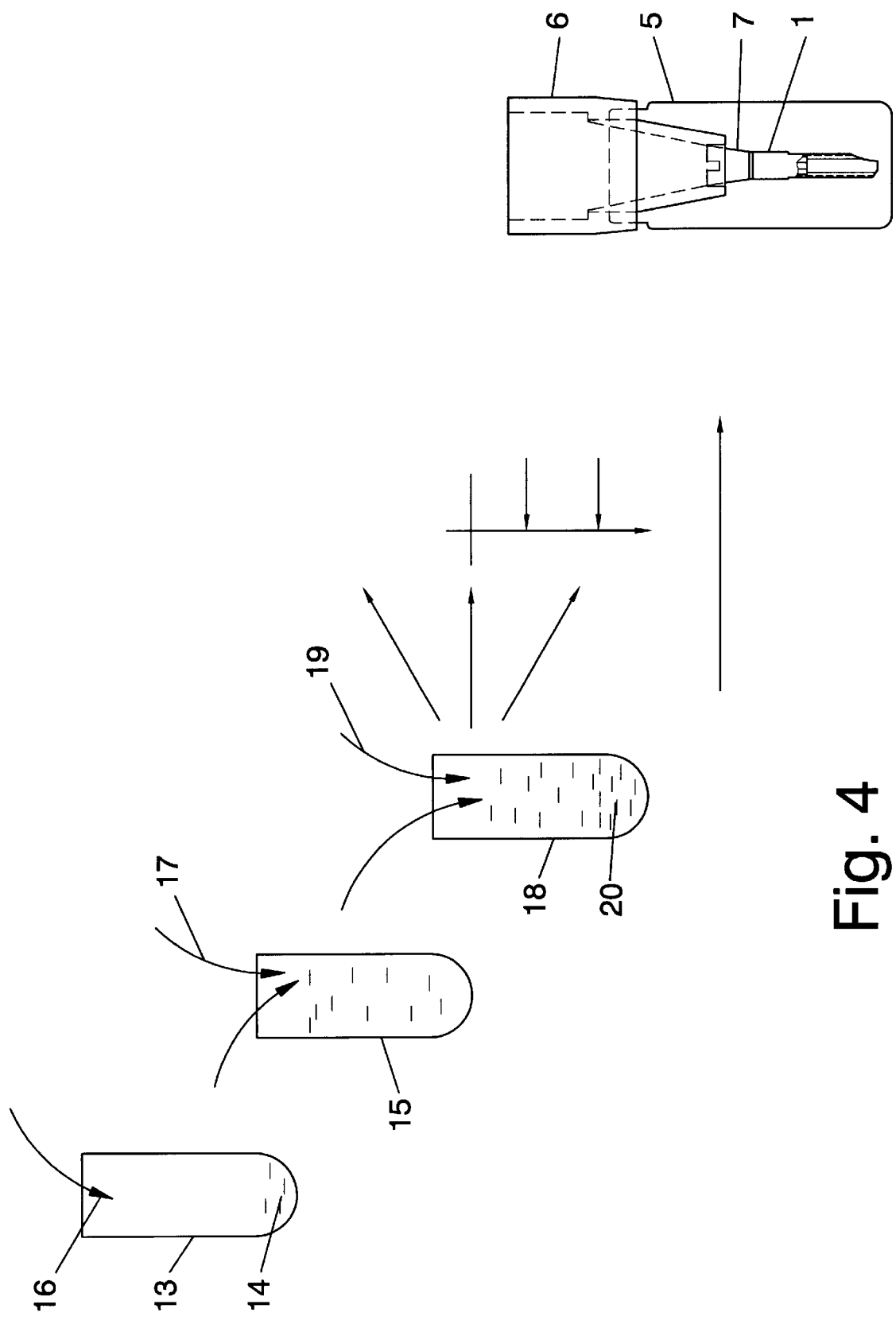

DENTAL IMPLANT AND OPERATIVE METHOD OF IMPLANTATION

OBJECT OF THE INVENTION

The following invention, as stated in the summary contained in this description, refers to a dental implant and operative method of implantation, being of the type comprising a body that is threaded into the jawbone and which is provided with a blind opening via which the appropriate securing and fastening bodies for the dental prosthesis are located, in such a way that the implant presented here has a hollow configuration with various angular cuts and/or drilled holes having been made in its base, the implants being individually presented in their respective receptacles, duly sterilized, in which, prior to their implantation, they are kept for a certain period of time in a bath of mononuclear cells washed with a McCOYS culture medium, these cells having been obtained from a blood extraction, duly treated, taken from the actual patient at the moment in which the implant is carried out.

In this way, and with the mononuclear cells introduced in the receptacle, the aim is to carry out an incubation of the implant for approximately half an hour at a temperature of 37° C., causing the cells to adhere to the implant and minimizing the risk of rejections, as well as facilitating osteo-integration by provoking rapid growth of the bone.

So, the container receptacle for the implant has a cap to which is joined the implant via an intermediate body, in such a way that in the implantation of the implant in the jawbone the cap itself is used as a tool in the operation of threading the implant into position so that the intermediate body is extracted along with the cap and next the extender bush is positioned threaded to the implant, as well as the remaining elements of the implant in itself, by means of the appropriate tools. In addition, in this way, at the same moment of positioning the implants, some pieces having the general shape of a hollow truncated cone are also positioned with some joining bars between them enabling the actual prosthesis of the patient to be positioned, duly adapted.

FIELD OF APPLICATION

The dental implant that is presented has application in odontology, being able to be used for the implant of a single dental piece or several pieces, in such a way that by using several implants the full denture can be secured, enabling it to be released in order to facilitate inspections of the state in which all the implants are to be found.

BACKGROUND OF THE INVENTION

With the passage of years, odontology has undergone considerable advances, aiming as far as possible to avoid extractions of dental pieces in such a way that, when it is necessary to do this, the extraction can be replaced by a fixed prosthesis and, in the extreme case of a total absence of dental pieces, by a fixed denture in relation to several points of the jawbone.

So, in the absence of dental pieces, temporary or permanent bridges are positioned, comprising elements of one or more artificial teeth fixed to a support that rests on the natural contiguous teeth.

If there are a considerable number of dental pieces missing, their replacement is done by means of a partial denture, while if the absence of dental pieces is total, then full dentures are resorted to.

In such a way, the drawbacks displayed by dentures that are not fixed are considerable and, since some time ago now, the trend has been towards prostheses that are fixed in position.

So, we can mention European Patent No. 126,624, which claims priority of Spanish Utility Models 272,292 and 279,140, in which separate fixed dental implants are claimed one of them comprising of the assembly of a pair of bodies, one of them being provided at one of its ends with an external thread for being secured to the jawbone, while in relation to its other end it has a central axial opening via which is introduced an end of the second body bearing the dental prosthesis, the two being secured together by pressure.

The axial central opening of the body fixed to the jawbone is made according to two diameters, the outer one being larger and being provided with an annular groove close to the section of greater diameter, with this threaded body also being provided with a annular groove in its free base into which is located an O-ring joint.

In the same way, the body bearing the dental prosthesis has its end embedded into that prosthesis and is provided with two annular projections, while its emergent cylindrical end has an staggered undercut in accordance with the internal diameters of the threaded body. An annular projection also existing, located in the smaller diameter end close to the staggering where an O-ring joint is located, partially introduced into the internal annular groove corresponding to the threaded body.

Likewise, the second implant is composed of two independent pieces, one of which is fixed to the jawbone and the other, bearing the prosthesis, is secured to the first by pressure, the body threaded to the jawbone displaying a central axial opening according to two diameters, the more external section of smaller diameter being provided with a thread and the larger diameter section close to where the smaller diameter arises having an annular recess, while the second body has a general shape of a cylinder, having an annular undercut in relation to the position of the prosthesis and a second undercut, also annular, close to its free base.

The union of both bodies will be done by providing the pair of undercuts made in the cylindrical body bearing the prosthesis with their respective O-rings which, when that body is fitted under pressure to the body threaded to the jawbone, will remain in relation to the annular undercut made in the section of larger diameter close to the threaded section of smaller diameter and in relation to its upper base.

So, the system of both is based on the resolution of forces materialized by the pair of O-rings giving the body bearing the prosthesis a movement similar to that of a natural tooth.

In the actual processing of said European Patent, British Patent 2,063,680, European Patent 0000549 and U.S. Pat. Nos. 4,290,255 and 1,397,067 were all regarded as antecedents, these last two merely belonging to the technical field.

In relation to British Patent 2,063,680, we can state that it claims an implant for the jawbone, comprising the union of three elements, which are intimately related to each other at the same time as one of them, the most external, is integral with the jawbone, in such a way that the implant becomes a single piece without any system of resolution of forces.

On the other hand, European Patent 0000549 claims an endoprosthesis comprising a cylindrical body provided on the inside with axial slots and whose outer surface is provided with a thread, the upper end of it being finished in a conical shape.

This body is intimately joined by a solid body provided on its outer surface with certain axial slots complementary to the inner slots of the external body, thereby defining an integral body that behaves as if it were a single body, in such a way that it does not display any system of resolution of forces either.

We can also mention Invention Patent P9602451, from the same applicants as this current paper, which claims a "dental implant" that comprises a shaft that is fixed to the body to which the prosthesis is attached and an extender bush fixed to the body of the implant, this shaft being traversed by the extender body in such a way that with respect to its internal end the shaft displays a pair of radial projections in a diametric position to each other, which remain in relation to the corresponding undercuts made in the internal end of the extender body.

Moreover, in order to permit ferruling the implants following their immediate insertion, some pieces having the general shape of a truncated cone are joined to the bodies receiving the prosthesis by means of a screw, these pieces displaying one or several radial threads for the securing of certain studs that make them integral to each other.

In addition, as is well known in haematology, starting from a blood extraction, preferably peripheral, conducted in large hospitals or specialized laboratories, mononuclear cells can be obtained by means of adequate treatment requiring time and cell growth accelerators. These cells can then be used in surgical operations to be performed on the actual patient later on, preferably in implantology or transplants, thereby achieving an increase in these cells.

DESCRIPTION OF THE INVENTION

This present report describes a dental implant and an operative method of implantation being of the type of implant comprising a body that is threaded into the jawbone via which the appropriate securing and fastening bodies for the dental prosthesis are located, characterized in that the implant body displays an axial cavity along its entire length and that its internal base for implantation displays drilled holes and/or angular cuts in its lateral surface that define end tabs. The implants are presented individually in their respective sterilized receptacles, being joined to the cap body of the receptacle via an intermediate body, the cap body defining a cavity with respect to its external base, in which is housed a body made of rubber or similar material, the cap body of the receptacle being provided with one or several traversing openings for accessing the internal cavity of the receptacle in which the implant is arranged which, prior to its implantation, is immersed in a bath of mononuclear cells with a McCOYS culture medium for a defined period of time and at a defined temperature.

The cap body of the receptacle for individually housing the implants, displays an internal truncated conical extension, the internal base of which is made to form a cavity with a diametric projection, to which the implant body is attached via the intermediate body for joining with the cap, while the lateral truncated conical surface presents one or various traversing openings via which it is possible to introduce an injector needle containing mononuclear cells washed in a McCOYS culture medium, obtained from a peripheral blood extraction, duly treated, taken from the actual patient on whom the implant is going to be performed.

Of course, the union of the intermediate body with the cap body of the receptacle will be able to be made by different means, since all in all it is a matter of creating a joint between both that will permit them to be handled.

Moreover, with the operative method that forms the object of the present invention, the separation and subsequent growth of the mononuclear cells is achieved quickly and operatively in small clinics without needing specialized laboratories, and this can be done at the moment when the operation is being performed at local level, without having to be admitted to a hospital.

So, once blood has been extracted from the patient on whom the implant is going to be performed, by means of the use of receptacles provided with an anticoagulant (for example, citrate), at the moment in which it is going to be handled, the blood is emptied into a receptacle to which the same quantity of serum has been added and this mixture is then emptied into a receptacle containing a cellular separator of density 1077 (e.g., ficoll). It is then centrifuged for a predefined length of time in order to obtain a division into three layers, the lower one of red corpuscles, the central one of mononuclear cells (of density 1077), and the upper layer of plasma.

Once the central layer of mononuclear cells has been separated, it is washed once with McCOYS culture medium in order to eliminate both the ficoll as well as other residues that might have come from the previous treatment, and a second wash is performed with a MCCOYS culture medium. It is then introduced into the receptacle containing the implant body or bodies that are going to be used.

After that, it is then incubated for a short predefined time at 37° C. in order to produce growth and adhesion of the mononuclear cells to the implant body, and it is then ready for its immediate implantation into the body of the patient.

The implant body, with the mononuclear cells adhered to it, is implanted by means of the actual cap body in the corresponding opening in the jawbone, permitting the subsequent positioning of all the components for the securing and fixing of the prosthesis by means of the appropriate tools.

So, the implant body will remain implanted in the jawbone with the intermediate body being withdrawn along with the cap body, so that the shaft with the extender bush and the body to which the prosthesis is fixed can then be positioned. There is the possibility, as claimed in patent P9602451, that in the case of dealing with several implants, a piece can be attached to the bearer bodies of the prosthesis between which some bars are fitted to which the patient's actual denture is positioned at the same instant, thus permitting the patient to leave the dentist's surgery with the own artificial denture already positioned.

In order to complement the description that is going to be given below, and with the aim of aiding a better understanding of the characteristics of the invention, this description is accompanied by a set of plans in which figures, the most characteristic details of the invention are represented, in a way that is intended to be illustrative only, rather than restrictive.

BRIEF DESCRIPTION OF THE DRAWINGS

FIG. 1. Shows a view of a container receptacle for an implant, the receptacle of which can be injected a solution of mononuclear cells by means of a McCOYS culture medium in order to leave the implant in a bath of that solution.

FIG. 2. Shows a cross-sectioned view, taken along a longitudinal diametric plane of an implant body, in which it can be seen how the implant has a hollow structure and how its internal end with respect to its position in the jawbone displays certain angular cuts.

FIG. 3. Shows a cross-sectioned view, taken along a longitudinal diametric plane of the container receptacle for the implant, showing an exploded view with the cap and a plug body made of rubber or similar.

FIG. 4. Shows a view of the different phases of the operative method for the preparation of an implant for its implantation, having previously been kept in a bath of mononuclear cells with a McCOYS culture medium so that these cells can become adhered to it.

DESCRIPTION OF AN EMBODIMENT OF THE INVENTION

With regard to the figures mentioned above and in accordance with the numbering adopted, we can see how the implant body 1 displays a central axial cavity 2 along its entire length and in its internal base with respect to its implantation displays certain angular cuts 3 having as well the securing thread 4 for attachment to the jawbone. The implant body 1 is structured for the assembly of the elements relating to the implant for the securing and fixing of the dental prosthesis. The angular cuts 3 can be replaced by a series of holes.

In order to facilitate the handling of the implants, they come individually presented in their corresponding sterilized receptacles 5, in such a way that the implant bodies 1 are joined to the actual cap 6 of the receptacle by means of an intermediate body 7, with the cap itself 6 of the receptacle being used as a tool for implantation in the hole made in the jawbone for that purpose.

For this, the cap 6 of the receptacle 5 is in general defined by a cylindrical section and an internal truncated conical extension in such a way that the truncated conical extension that is introduced into the receptacle and the intermediate body 7 for joining with the implant body 1 to the cap 6 are materialized with respect to its internal smaller base, for which the cap has an undercut 8 with a diametric projection 9, this projection 9 coupling and fitting to an undercut made in the intermediate body so as to permit it to be pulled along when the cap is rotated at the moment of the implantation. Of course, the union of the intermediate body 7 with the cap 6 can be produced in different ways, at all times bearing in mind that the implantation of the implant body 1 into the jawbone will be done by means of the cap. This union can be achieved by means of a polygonal cavity or other similar means.

Likewise, the cap body 6 displays a cavity according to the two sections defining it, in such a way that, with respect to the lateral truncated conical surface, it displays a series of traversing openings 10, permitting the passage of an injector needle, while in the cavity 11 relative to the external hollow cylindrical section, it displays a plug body 12 made of rubber or similar material in order to leave the assembly sealed.

With the operative method forming the object of this invention, the aim is to obtain in small clinics, the separation and subsequent growth of mononuclear cells in a quick and operative manner, without requiring specialized laboratories, and being able to do so at the moment in which the operation of implantation is going to be carried out at local level without having to be admitted to a hospital.

So, a blood extraction 16 is taken in the conventional manner from the patient who is going to receive the implant, by means of the use of receptacles 13 provided with an anticoagulant 14 (e.g., citrate). At the moment of handling it is emptied into the receptacle 15 to which is added the same quantity of serum 17, this mixture is next emptied into a receptacle 18 containing a cell separator 19 of density 1077 (e.g. ficoll); the mixture 20 is centrifuged for a predetermined length of time in order to obtain a division into three layers, the lower one comprising red corpuscles; the central one, mononuclear cells of density 1077 and the upper one, plasma.

Once the central layer of mononuclear cells has been separated it is washed once in a McCOYS culture medium in order to eliminate both the ficoll as well as other residues that might be left over from the previous treatment, and then a second wash is performed with a McCOYS culture medium and it is then introduced into the container receptacle 5 of the implant body 1 that is going to be used.

Of course, several receptacles can be used simultaneously with their corresponding implant bodies 1, depending on the number of implants to carry out.

Later on, it is incubated for a predetermined length of time at 37° C. in order to provoke the growth and adhesion of the mononuclear cells to the implant body 1, which is then ready for its immediate implantation into the patient.

In order to proceed to the implantation of the implant body 1 with mononuclear cells adhered to it, the procedure will be by means of the cap body 6, the implant body 1 being implanted in the corresponding opening made in the jawbone for that purpose, and the intermediate body 7 being extracted with the cap 6, and leaving the implant body 1 prepared for receiving the shaft with the extender bush and other components by means of the appropriate tools.

What is claimed is:

1. A dental implant comprising an implant body that is to be threaded into a jawbone and in which securing and fastening bodies for a dental prosthesis are located, the implant body having an axial cavity along its entire length, wherein an internal base of said implant body having a lateral surface including at least one element for implantation selected from the group consisting of holes, angular cuts and combinations thereof, so as to define end tabs;

a sterilized receptacle in which said implant body is housed, a cap body arranged at open end of said receptacle, said cap body having an intermediate body arranged at a lower portion of said cap body and joined to said implant body, wherein said cap body has a cavity with respect to an external base in which is housed a body made of an elastomeric material; said cap body having at least one traverse opening for accessing of an internal cavity of the receptacle where said implant body is housed and immersed in a bath of mononuclear cells with a McCOYS culture medium.

2. A dental implant according to claim 1 wherein said cap body comprises an internal truncated-conical extension shape having an internal base comprising a cavity with a diametric projection to which a first end of the intermediate body is joined, and wherein said intermediate body is joined at a second end to the implant body; said truncated-conical extension shape having a lateral surface provided with at least one traverse opening for introducing a needle of an injector containing mononuclear cells washed in a McCOYS culture medium.

3. A method of implantation of a dental implant, comprising the steps of:

(a) storing an extraction of peripheral blood of a patient receiving an implant in an extraction receptacle provided with an anticoagulant, (b) emptying a predetermined quantity of the blood into a receptacle to which has been added an identical quantity of serum, (c) separating said cells by providing a receptacle containing a cell separator of a density 1077, which is centrifuged in order to separate it into different layers of blood components, (d) extracting a layer of mononuclear cells separated in step (c) for carrying out two consecutive washes in a McCOYS culture medium which is introduced into a receptacle containing the implant body to be implanted, (e) incubating for a predetermined period of time at a constant temperature of 37° C. the mononuclear cells introduced into a receptacle in step (d), so that the mononuclear cells become adhered to the implant body, wherein said implant body is ready for implantation.

4. The method of implantation of a dental implant according to claim 3, further comprising:

(f) implanting the implant body with the mononuclear cells adhered into an opening in the jawbone by means of a cap body joined to the receptacle housing said dental implant, and (g) performing a subsequent positioning of all securing and fastening components of a unitary or complete prosthesis.

5. The method of implantation of a dental implant, according to claim 3, wherein the implant body of said dental implant is threaded into a jawbone via in which securing and fastening bodies for the dental prosthesis are located, wherein the implant body comprises an axial cavity along its entire length, and whose internal base has a lateral surface having at least one element for implantation selected from the group consisting of holes, angular cuts and combinations thereof that define end tabs; the implant being housed in a sterilized receptacle, and the implant body being joined to a first end of an intermediate body, and cap body of said receptacle being joined to a second end of the intermediate body, said cap body being provided with, a cavity with respect to an external base in which is housed a body made of an elastomeric material; the cap body of the receptacle also being provided with at least one traverse opening for accessing an internal cavity of the receptacle where the implant is housed and immersed in a bath of mononuclear cells with a McCOYS culture medium.

6. The method of implantation of a dental implant according to claim 5, wherein the cap body of the receptacle for housing said dental implant is provided with an internal truncated-conical extension having internal base comprises a cavity with a diametric projection to which the implant body is joined to the first end of the intermediate body; and wherein the truncated-conical extension has a lateral surface being provided with at least one traverse opening for introducing a needle of an injector containing mononuclear cells washed in a McCOYS culture medium.

\* \* \* \* \*